(12) United States Patent
Koppel et al.

(10) Patent No.: US 11,457,827 B2
(45) Date of Patent: *Oct. 4, 2022

(54) DETECTION OF PATENT DUCTUS ARTERIOSUS USING PHOTOPLETHYSMOGRAPHY

(71) Applicants: The Feinstein Institutes For Medical Research, Manhasset, NY (US); Jerusalem College of Technology, Jerusalem (IL)

(72) Inventors: Robert Koppel, West Hempstead, NY (US); Meir Nitzan, Bet El (IL)

(73) Assignees: The Feinstein Institutes For Medical Research, Manhasset, NY (US); Jerusalem College of Technology, Jerusalem (IL)

( * ) Notice: Subject to any disclaimer, the term of this patent is extended or adjusted under 35 U.S.C. 154(b) by 364 days.

This patent is subject to a terminal disclaimer.

(21) Appl. No.: 16/848,658

(22) Filed: Apr. 14, 2020

(65) Prior Publication Data
US 2020/0237241 A1 Jul. 30, 2020

Related U.S. Application Data

(63) Continuation of application No. 15/505,696, filed as application No. PCT/US2015/047162 on Aug. 27, 2015, now Pat. No. 10,653,326.

(60) Provisional application No. 62/134,619, filed on Mar. 18, 2015, provisional application No. 62/042,823, filed on Aug. 28, 2014.

(51) Int. Cl.
*A61B 5/024* (2006.01)
*A61B 5/02* (2006.01)
*A61B 5/00* (2006.01)
*A61B 5/349* (2021.01)
(Continued)

(52) U.S. Cl.
CPC ...... *A61B 5/02416* (2013.01); *A61B 5/02007* (2013.01); *A61B 5/349* (2021.01); *A61B 5/6801* (2013.01); *A61B 5/7282* (2013.01); *A61B 5/352* (2021.01); *A61B 5/366* (2021.01); *A61B 5/6814* (2013.01); *A61B 5/6825* (2013.01);
(Continued)

(58) Field of Classification Search
CPC ............ A61B 5/02416; A61B 5/02007; A61B 5/6801; A61B 5/7282; A61B 5/6814; A61B 5/6825; A61B 5/6829; A61B 2503/04; A61B 2503/045
See application file for complete search history.

(56) References Cited

U.S. PATENT DOCUMENTS 6,331,162 B1 12/2001 Mitchell
6,334,065 B1 12/2001 Al-Ali et al.
(Continued)

OTHER PUBLICATIONS

PCT International Search Report and Written Opinion dated Nov. 27, 2015 for PCT International Patent Application No. PCT/US2015/047162, 11 pages.

(Continued)

*Primary Examiner* — Jonathan T Kuo
(74) *Attorney, Agent, or Firm* — Amster, Rothstein & Ebenstein LLP

(57) ABSTRACT

Methods and systems are described for detecting the likelihood of patent ductus arteriosus (PDA) in an infant using electrocardiogram and photoplethysmographic pulse signals obtained from the upper body and foot of the infant.

8 Claims, 7 Drawing Sheets

(51) Int. Cl.
*A61B 5/352* (2021.01)
*A61B 5/366* (2021.01)

(52) U.S. Cl.
CPC ......... *A61B 5/6829* (2013.01); *A61B 2503/04* (2013.01); *A61B 2503/045* (2013.01)

(56) References Cited

U.S. PATENT DOCUMENTS

| | | |
|---|---|---|
| 10,376,154 B2 | 8/2019 | Koppel et al. |
| 10,653,326 B2 * | 5/2020 | Koppel ................ A61B 5/7282 |
| 2004/0220631 A1 | 11/2004 | Burnes et al. |
| 2008/0183232 A1 | 7/2008 | Voss et al. |
| 2010/0332173 A1 | 12/2010 | Watson et al. |
| 2011/0066045 A1 | 3/2011 | Moon et al. |

OTHER PUBLICATIONS

Goudjil et al., "Noninvasive Technique for the Diagnosis of Patent Ductus Arteriosus in Premature Infants by Analyzing Pulse Wave Phases on Photoplethysmography Signals Measured in the Right Hand and the Left Foot," PLoS ONE, vol. 9, No. 6, Jun. 2014, 14 pages.
Oishi et al., "Monitoring Neonatal Peripheral Circulation by Electrocardiogram-to-Oximeter Pulse Velocity," Pediatric Research, vol. 33, No. 6, 1993, pp. 653-657.

* cited by examiner

DETECTION OF PATENT DUCTUS ARTERIOSUS USING PHOTOPLETHYSMOGRAPHY

CROSS-REFERENCE TO RELATED APPLICATIONS

This application is a continuation of U.S. patent application Ser. No. 15/505,696, filed Feb. 22, 2017, now allowed, which is a U.S. national stage entry under 35 U.S.C. § 371 of PCT International Patent Application No. PCT/US2015/047162, filed Aug. 27, 2015, which claims the benefit of U.S. Provisional Patent Application No. 62/042,823, filed Aug. 28, 2014 and of U.S. Provisional Patent Application No. 62/134,619, filed Mar. 18, 2015, the contents of which are incorporated herein by reference into the subject application.

BACKGROUND OF THE INVENTION

Throughout this application various publications are referred to in parentheses. Full citations for these references may be found at the end of the specification. The disclosures of these publications are hereby incorporated by reference in their entirety into the subject application to more fully describe the art to which the subject invention pertains.

Patent ductus arterious (PDA) is a common problem causing significant morbidity and mortality in preterm infants. The ductus arteriosus is a blood vessel that connects the aorta and pulmonary artery and plays an important role in fetal life. In full-term newborn infants, the ductus arteriosus constricts by 24 to 48 hours of life. However, in preterm infants, the ductus arteriosus often remains patent. Persistent patent ductus arteriosus is a common problem with rates of 40-55% encountered in preterm infants <29 weeks gestation (McNamara and Sehgal 2007). A PDA with a significant left to right shunting can lead to increased neonatal morbidity such as respiratory distress, cardiac failure, low blood pressure, and decreased peripheral organ perfusion, and leads to an increased incidence of intraventricular hemorrhage, necrotizing enterocolitis and chronic lung disease (Sehgal and McNamara 2012). The important aspect of assessment of a PDA is whether the degree of left to right shunting across the PDA is of hemodynamic significance and will therefore require treatment (Evans et al. 2012b). Assessment of the significance of the ductal flow is challenging. The amount of transductal flow between the descending aorta and the pulmonary artery is dependent not only on the ductal diameter but also on the difference between the systemic and pulmonary vascular resistance (McNamara and Sehgal 2007). The physiologic effects include increased systemic to pulmonary blood flow during systole and reversal of normal aortic flow during diastole called ductal steal. The combination of ductal steal and low diastolic pressure results in regional hypoperfusion (Noori 2010, Evans et al. 2012a). Diastolic ductal steal phenomenon is seen in hemodynamically significant patent ductus arteriosus (HSDA) and resolves after ductal closure (Evans et al. 2012a). Symptomatic shunting through a PDA has been associated with worse respiratory outcomes (Evans 1995).

The current clinical evaluations, electrocardiogram (ECG) and chest X-ray (CXR) findings, are neither accurate nor specific. Doppler echocardiography has proved to be better than clinical examination in grading PDAs (McNamara and Sehgal 2007). It is unlikely that optimum timing of therapeutic intervention may be predicted by postnatal age, as the determinants of a hemodynamically significant ductal shunt include transductal resistance and physiological modifiers. The difficulty in precisely separating the pathological ductus arteriosus from the innocent ductus arteriosus may be due to the lack of scientific evidence of benefit or causality (McNamara and Sehgal 2007, Sehgal and McNamara 2012). The ensuing effect is medical ambiguity and an unending dispute of whether these neonates have to be treated, the optimum timing of treatment and implications to when intervention is most effective. The nature of the confusion is thought to relate to limitations and/or delays in appraisal of ductal significance (Sehgal and McNamara 2012). Trials to date have focused on time, method and duration of intervention but not to scale the hemodynamic significance. The conventional guide by which ductal significance has been ascertained is transductal diameter but this might not imply significance in some situations.

Recent literature has questioned the beneficial effects of therapeutic intervention. The reasons for this apparent lack of effect may relate to a lack of relationship of a HSDA to neonatal outcomes due to inaccurate assignment of hemodynamic significance. Other than clinical parameters and echocardiographic evaluation, there are no other non-invasive clinical tools to help assess this common but difficult diagnostic entity from a therapeutic standpoint.

Echocardiographic evaluation has been considered the gold standard for diagnosis of a patent ductus arteriosus, but quantifying the size of ductal flow which leads to negative consequences remains a problem (McNamara and Sehgal 2007, Evans et al. 2012a). The decision to treat is based on echocardiographic documentation of a left to right transductal shunt with quantifiable hemodynamic effects leading to clinical instability. The current definition of HSDA is not adequate since it is entirely reliant on size (McNamara and Sehgal 2007). A transductal diameter of >1.5 mm has been proposed as significant since data from a small study with a sample size of 50 suggest that beyond this cut-off, end organ hypoperfusion occurs (Kluckow and Evans 1995, Evans 1995). This definition is incomplete because it does not take into consideration the maturational status of the patient and other biological factors that may account for unpredictability in clinical presentation. The lack of a uniform approach is a key hindrance towards better comprehension of the clinical effect of a patent ductus.

Description of the transductal flow pattern and direction are important in directing treatment decisions. However, flow indicators have a lower predictive value for therapeutic interventions because apart from ductal diameter, flow is dependent on the relative systemic and pulmonary vascular resistance which are highly variable in preterm infants with respiratory problems. In neonates with pulmonary hypertension, ductal flow is either pure right to left when pulmonary arterial pressure is suprasystemic or bidirectional (right to left during systole and left to right during diastole when it is equal to systemic arterial pressure). Prior studies have demonstrated the duct as closing/restrictive or unrestrictive and pulsatile according to pulse wave Doppler flow patterns. A HSDA will have a large left to right with pulsatile flow pattern and peak velocity at end systole. The peak velocity at the end diastole is usually very low. This implies that the relative pulmonary and aortic pressures are equal at the end of diastole. The peak systolic velocity is usually less than 1.5 m/s when the ductus is unrestrictive. As the ductus constricts, flow velocity increases as blood accelerates across a narrower vessel leading to a reduction in the peak systolic/diastolic ratio. Computing the volume of transductal flow would offer the most precise assessment of hemodynamic compromise. However, the calculation is not practical with conventional two dimensional techniques due to ductal tortuosity, changes in the transductal diameter across it course and the turbulent rather than laminar nature of flow.

Other echocardiographic parameters have been used to assess the amount of pulmonary blood flow. There are no direct measures of increased pulmonary blood flow; however, left heart size and flow are useful surrogate determinants of the magnitude of flow and its impact. The Left Atrial/Aorta (LA/AO) ratio has been used in several studies to evaluate the significance of ductal shunting. Evans and Iyer (1995) showed that a LA/AO ratio of >1.4 is suggestive of a HSDA. This ratio derived using M-mode imaging from a long axis approach is the most well recognized surrogate of ductal significance and was first described by Silverman et al. in 1974. Independently these markers have poor sensitivity and specificity, which may be related to a number of factors. These include patient related factors such as hydration, left ventricle performance or transatrial shunt and operator dependent factors, which may lead to over or underestimation of these single dimensional measurements (Evans et al. 2012a).

Newer echocardiographic assessment to determine a clinically significant PDA have been to profile the pulmonary artery flow pattern, left heart flow quantification, left ventricular output, LVO/SVC ratio and flow velocity in the LPA, all of which have been studied using small sample size (El Hajjar et al. 2005). Pulmonary artery flow is typically laminar and exclusively systolic with maximum velocity of about 1.5 m/s. The presence of HSDA leads to diastolic flow in the main and branch pulmonary arteries with a turbulent systolic pattern. The magnitude of diastolic flow in the main and left branch pulmonary artery correlates well with the magnitude of left to right shunt, but these studies do not address the clinical impact of this finding (Evans et al. 2012a,b). Quantification of pulmonary venous flow may provide the best measure of pulmonary overcirculation; however, accurate estimation of flow is challenging due to the tortuosity of the veins and variability of flow between the veins (Evans et al. 2012a).

Previous approaches for detection of PDA remain unsatisfactory. Vital signs and physical examination are neither sensitive nor specific for detection of PDA and echocardiography, although non-invasive, is disruptive to the patient, expensive, and only describes the status of the ductus at one point in time. This leaves the clinician with uncertainty about ductal shunting between echocardiograms.

Photoplethymography (PPG) is an easy and inexpensive optical technique that can be used to detect change in blood volume in the microvascular bed of tissue. It is frequently utilized to make non-invasive measurements at the skin surface. In photoplethysmography, the emitted light passes through the skin and is reflected, absorbed, and scattered by the tissue and blood (Sahni 2012). The amount of the modulated transmitted or reflected light that reaches the photodetector is measured, and the changes in the photodetector current are presumed to be due to blood volume changes underneath the probe. The systolic increase in the arterial blood pressure is accompanied by an increase in arterial blood volume resulting in reduced light transmission (Nitzan et al. 2009). These variations are electronically amplified and recorded as a voltage signal called the photoplethysmograph (Sahni 2012). The PPG waveform comprises a physiological waveform attributed to cardiac synchronous changes in the peripheral blood volume with each heart beat and is superimposed on a varying baseline with various lower frequency components such as respiration, sympathetic nervous system and thermoregulation. Changes in the pulse shape characteristics can yield valuable diagnostic information about the cardiovascular system. PPG has been experimentally used to assess the viscoelastic properties of blood vessels including the volume elastic modulus of finger arteries, which is the arterial pulse pressure related to PPG volume change at specific transmural pressures (Elgendi 2012, Allen 2007). PPG has been used to calculate pulse wave phases, and the difference between the right hand and left foot phases has been reported to correlate with PDA in a group of 56 subjects (Goudjil et al. 2014). Oishi et al. (1993) reported monitoring neonatal peripheral circulation by electrocardiogram-to-oximeter pulse velocity in three subjects with different clinical conditions.

The present invention addresses the need for improved methods and apparatus for detecting patent ductus arteriosus (PDA) and monitoring ductus closure in newborns using photoplethysmographic measurements.

SUMMARY OF THE INVENTION

The present invention provides methods for detecting the likelihood of patent ductus arteriosus (PDA) in an infant comprising a) obtaining or receiving electrocardiogram (ECG) signals from the infant; b) obtaining or receiving photoplethysmographic (PPG) signals from a site on the upper body (UB) of the infant, and optionally from a foot (F) of the infant; c) determining, for each PPG pulse the PPG pulse amplitude (AM) between the end-diastolic maximum and the following minimum of systolic decrease for the UB PPG pulses; d) determining the mean of one or more of the following parameters for a plurality of the PPG pulses in the selected section: (i) a relative pulse amplitude (rAM) by dividing the AM by the systolic decrease minimum to obtain a rAM for the upper body (rAM-UB) PPG pulses; (ii) a pulse transit time (PTT-UB) between an R wave of the ECG and the onset of systolic decrease for the corresponding UB PPG pulse; (iii) a ratio PTT-UB/rAM-UB between the pulse transit time (PTT-UB) and the relative pulse amplitude for the UB (rAM-UB) PPG pulse; (iv) a ratio rAM-UB/PTT-UB between the relative pulse amplitude for the UB (rAM-UB) PPG pulse and the pulse transit time (PTT-UB); (v) a pulse transit time (PTT-F) between an R wave of the ECG and the onset of systolic decrease for the corresponding F PPG pulse; and (vi) a time delay (TD) between the onset of systolic decrease for the UB PPG pulse and the onset of systolic decrease for the corresponding F PPG pulse; and e) detecting the likelihood of a patent ductus arteriosus (PDA) in the infant if one or more of: the relative pulse amplitude for the UB (rAM-UB) is elevated above normal, the pulse transit time (PTT-UB) is decreased below normal; the ratio PTT-UB/rAM-UB is decreased below normal, the ratio rAM-UB/PTT-UB is elevated above normal, the pulse transit time (PTT-F) is decreased below normal; or the time delay (TD) of PPG pulses between the UB and F is elevated above normal.

The invention also provides systems for detecting the likelihood of patent ductus arteriosus (PDA) in an infant comprising a photoplethysmograph, one or more computing devices comprising one or more processors, a memory unit, a display device, and a computer-readable storage medium including computer-readable code that is read by the one or more processors to perform the method described above.

DETAILED DESCRIPTION OF THE INVENTION

Figure 1A:
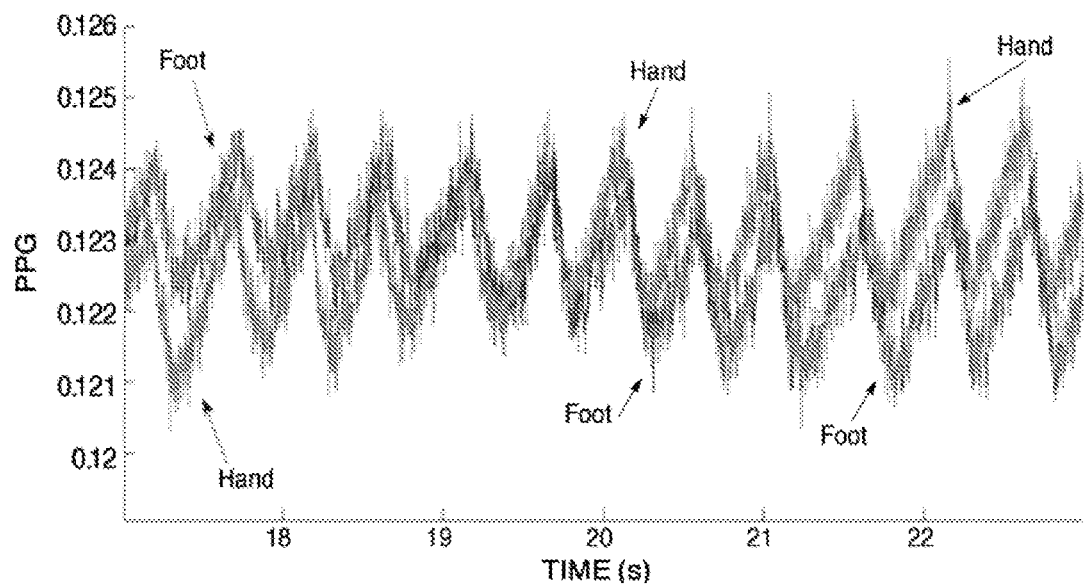
FIG. 1A. Examples of raw, unsmoothed photoplethysmographic (PPG) curves from an infant with PDA.

The invention provides a method for detecting the likelihood of a patent ductus arteriosus (PDA) in an infant comprising:
  a) obtaining or receiving electrocardiogram (ECG) signals from the infant;
  b) obtaining or receiving photoplethysmographic (PPG) signals from a site on the upper body (UB) of the infant, and optionally from a foot (F) of the infant;
  c) determining, for each PPG pulse the PPG pulse amplitude (AM) between the end-diastolic maximum and the following minimum of systolic decrease for the UB PPG pulses;
  d) determining the mean of one or more of the following parameters for a plurality of the PPG pulses in the selected section:
    (i) a relative pulse amplitude (rAM) by dividing the AM by the systolic decrease minimum to obtain a rAM for the upper body (rAM-UB) PPG pulses;
    (ii) a pulse transit time (PTT-UB) between an R wave of the ECG and the onset of systolic decrease for the corresponding UB PPG pulse;
    (iii) a ratio PTT-UB/rAM-UB between the pulse transit time (PTT-UB) and the relative pulse amplitude for the UB (rAM-UB) PPG pulse;
    (iv) a ratio rAM-UB/PTT-UB between the relative pulse amplitude for the UB (rAM-UB) PPG pulse and the pulse transit time (PTT-UB);
    (v) a pulse transit time (PTT-F) between an R wave of the ECG and the onset of systolic decrease for the corresponding F PPG pulse; and
    (vi) a time delay (TD) between the onset of systolic decrease for the UB PPG pulse and the onset of systolic decrease for the corresponding F PPG pulse; and
  e) detecting the likelihood of a patent ductus arteriosus (PDA) in the infant if one or more of:
    the relative pulse amplitude for the UB (rAM-UB) is elevated above normal,
    the pulse transit time (PTT-UB) is decreased below normal;
    the ratio PTT-UB/rAM-UB is decreased below normal,
    the ratio rAM-UB/PTT-UB is elevated above normal,
    the pulse transit time (PTT-F) is decreased below normal; or
    the time delay (TD) of PPG pulses between the UB and F is elevated above normal.

As used in the comparisons "elevated above normal" and "decreased below normal" the term "normal" refers to the values of the parameters obtained from infants with a closed ductus arteriosus.

As used herein, the term "upper body" ("UB") is meant to include the portion of the body including and above the level of the arms. Examples of skin sites that can be used, include but are not limited to, the hand (H), in particular the right hand (RH), the forehead (FH) and an earlobe (EL). Examples of sites that can be used on the foot (F) include but are not limited to a toe (T). Preferably, PPG signals are obtained from both the upper body and the foot (F) of the infant.

The invention also provides a system for detecting the likelihood of patent ductus arteriosus (PDA) in an infant comprising a photoplethysmograph having one or more channels, one or more computing devices comprising one or more processors, a memory unit, a display device, and a computer-readable storage medium including computer-readable code that is read by the one or more processors to perform a method comprising the steps of:
  a) obtaining or receiving electrocardiogram (ECG) signals from the infant;
  b) obtaining or receiving photoplethysmographic (PPG) signals from a site on the upper body (UB) of the infant, and optionally from a foot (F) of the infant;
  c) determining, for each PPG pulse the PPG pulse amplitude (AM) between the end-diastolic maximum and the following minimum of systolic decrease for the UB PPG pulses;
  d) determining the mean of one or more of the following parameters for a plurality of the PPG pulses in the selected section:
    (i) a relative pulse amplitude (rAM) by dividing the AM by the systolic decrease minimum to obtain a rAM for the upper body (rAM-UB) PPG pulses;
    (ii) a pulse transit time (PTT-UB) between an R wave of the ECG and the onset of systolic decrease for the corresponding UB PPG pulse;
    (iii) a ratio PTT-UB/rAM-UB between the pulse transit time (PTT-UB) and the relative pulse amplitude for the UB (rAM-UB) PPG pulse;
    (iv) a ratio rAM-UB/PTT-UB between the relative pulse amplitude for the UB (rAM-UB) PPG pulse and the pulse transit time (PTT-UB);
    (v) a pulse transit time (PTT-F) between an R wave of the ECG and the onset of systolic decrease for the corresponding F PPG pulse; and
    (vi) a time delay (TD) between the onset of systolic decrease for the UB PPG pulse and the onset of systolic decrease for the corresponding F PPG pulse; and e) detecting the likelihood of a patent ductus arteriosus (PDA) in the infant if one or more of:
   the relative pulse amplitude for the UB (rAM-UB) is elevated above normal,
   the pulse transit time (PTT-UB) is decreased below normal;
   the ratio PTT-UB/rAM-UB is decreased below normal,
   the ratio rAM-UB/PTT-UB is elevated above normal,
   the pulse transit time (PTT-F) is decreased below normal; or
   the time delay (TD) of PPG pulses between the UB and F is elevated above normal.

Also provided is a method for detecting the likelihood of a patent ductus arteriosus (PDA) in an infant comprising:
a) determining from photoplethysmographic (PPG) signals from a site on the upper body (UB) of the infant, and optionally from a foot (F) of the infant, for each PPG pulse, the PPG pulse amplitude (AM) between the end-diastolic maximum and the following minimum of systolic decrease for the UB PPG pulses;
b) determining the mean of one or more of the following parameters for a plurality of the PPG pulses in the selected section:
   (i) a relative pulse amplitude (rAM) by dividing the AM by the systolic decrease minimum to obtain a rAM for the upper body (rAM-UB) PPG pulses;
   (ii) a pulse transit time (PTT-UB) between an R wave of an electrocardiogram (ECG) from the infant and the onset of systolic decrease for the corresponding UB PPG pulse;
   (iii) a ratio PTT-UB/rAM-UB between the pulse transit time (PTT-UB) and the relative pulse amplitude for the UB (rAM-UB) PPG pulse;
   (iv) a ratio rAM-UB/PTT-UB between the relative pulse amplitude for the UB (rAM-UB) PPG pulse and the pulse transit time (PTT-UB);
   (v) a pulse transit time (PTT-F) between an R wave of the ECG and the onset of systolic decrease for the corresponding F PPG pulse; and
   (vi) a time delay (TD) between the onset of systolic decrease for the UB PPG pulse and the onset of systolic decrease for the corresponding F PPG pulse; and
c) detecting the likelihood of a patent ductus arteriosus (PDA) in the infant if one or more of:
   the relative pulse amplitude for the UB (rAM-UB) is elevated above normal,
   the pulse transit time (PTT-UB) is decreased below normal;
   the ratio PTT-UB/rAM-UB is decreased below normal,
   the ratio rAM-UB/PTT-UB is elevated above normal,
   the pulse transit time (PTT-F) is decreased below normal; or
   the time delay (TD) of PPG pulses between the UB and F is elevated above normal.

Also provided is use of photoplethysmographic (PPG) signals from a site on the upper body (UB) of an infant, and optionally from a foot (F) of the infant, and of electrocardiogram (ECG) signals from the infant, for detecting the likelihood of a patent ductus arteriosus (PDA) in the infant by a method comprising:
a) determining, for each PPG pulse the PPG pulse amplitude (AM) between the end-diastolic maximum and the following minimum of systolic decrease for the UB PPG pulses;
b) determining the mean of one or more of the following parameters for a plurality of the PPG pulses in the selected section:
   (i) a relative pulse amplitude (rAM) by dividing the AM by the systolic decrease minimum to obtain a rAM for the upper body (rAM-UB) PPG pulses;
   (ii) a pulse transit time (PTT-UB) between an R wave of the ECG and the onset of systolic decrease for the corresponding UB PPG pulse;
   (iii) a ratio PTT-UB/rAM-UB between the pulse transit time (PTT-UB) and the relative pulse amplitude for the UB (rAM-UB) PPG pulse;
   (iv) a ratio rAM-UB/PTT-UB between the relative pulse amplitude for the UB (rAM-UB) PPG pulse and the pulse transit time (PTT-UB);
   (v) a pulse transit time (PTT-F) between an R wave of the ECG and the onset of systolic decrease for the corresponding F PPG pulse; and
   (vi) a time delay (TD) between the onset of systolic decrease for the UB PPG pulse and the onset of systolic decrease for the corresponding F PPG pulse; and
c) detecting the likelihood of a patent ductus arteriosus (PDA) in the infant if one or more of:
   the relative pulse amplitude for the UB (rAM-UB) is elevated above normal,
   the pulse transit time (PTT-UB) is decreased below normal;
   the ratio PTT-UB/rAM-UB is decreased below normal,
   the ratio rAM-UB/PTT-UB is elevated above normal,
   the pulse transit time (PTT-F) is decreased below normal; or
   the time delay (TD) of PPG pulses between the UB and F is elevated above normal.

In one embodiment, the likelihood of a patent ductus arteriosus (PDA) in the infant is detected if one or more of: the relative pulse amplitude for the UB (rAM-UB) is elevated above normal, the ratio PTT-UB/rAM-UB is decreased below normal, the ratio rAM-UB/PTT-UB is elevated above normal, or the time delay (TD) of PPG pulses between the UB and F is elevated above normal.

The method can further comprise one or more steps of selecting a section of PPG pulses without movement noise for analysis, low-pass filtering PPG signals to reduce high frequency noise, and smoothing PPG signals using a moving average filter. In one embodiment, a parameter from 10-20 pulses is averaged to obtain a mean.

In one embodiment, infants with a closed ductus arteriosus have a mean rAM-UB of 1.5%. Tn different embodiments, a rAM-UB value above 2% or 2.1% or 2.2% or 2.3% or 2.4% or 2.6% is indicative that the infant has patent ductus arteriosus (PDA). In one embodiment, a rAM-UB value above a predetermined value in a range of 1.7% to 2.6% is indicative that the infant has patent ductus arteriosus (PDA). In one embodiment, a rAM-UB value above a predetermined value in a range of 1.7% to 2.0% is indicative that the infant has patent ductus arteriosus (PDA).

In one embodiment, infants with a closed ductus arteriosus have a mean PTT-UB of 69.0 ms. In one embodiment, a PTT-UB value below 55 ms is indicative that the infant has patent ductus arteriosus (PDA). In one embodiment, a PTT-UB value below a predetermined value in a range of 50 ms to 60 ms is indicative that the infant has patent ductus arteriosus (PDA).

In one embodiment, infants with a closed ductus arteriosus have a mean PTT-F of 89.0 ms. In one embodiment, a PTT-F value below 80 ms is indicative that the infant has patent ductus arteriosus (PDA). In one embodiment, a PTT-F value below a predetermined value in a range of 70 ms to 80 ms is indicative that the infant has patent ductus arteriosus (PDA).

In one embodiment, infants with a closed ductus arteriosus have a mean ratio PTT-UB/rAM-UB of 50 ms/%. In one embodiment, a PTT-UB/rAM-UB value below 30 ms/% is indicative that the infant has patent ductus arteriosus (PDA). In one embodiment, a PTT-UB/rAM-UB value below a predetermined value in a range of 25 ms/% to 35 ms/% is indicative that the infant has patent ductus arteriosus (PDA).

In one embodiment, infants with a closed ductus arteriosus have a mean ratio rAM-UB/PTT-UB of 24%/s. In one embodiment, a rAM-UB/PTT-UB value above 30%/s is indicative that the infant has patent ductus arteriosus (PDA). In one embodiment, a rAM-UB/PTT-UB value above a predetermined value in a range of 30%/s to 35%/s is indicative that the infant has patent ductus arteriosus (PDA).

In one embodiment, infants with a closed ductus arteriosus have a mean time delay (TD) of PPG pulses between the UB and F of 25 ms. In one embodiment, an UB-F TD value above 29 ms is indicative that the infant has patent ductus arteriosus (PDA). In one embodiment, an UB-F TD value above a predetermined value in a range of 29-40 ms is indicative that the infant has patent ductus arteriosus (PDA).

The method can also comprise obtaining echocardiographic measurements from the infant. One or more of the following parameters can be used in combination with rAM-UB or in place of rAM-UB: ratio left atrium diameter/aorta diameter, left pulmonary artery peak end diastolic velocity, and left ventricle shortening fraction.

Preferably, the photoplethysmograph has an infrared light source. In different embodiments, the photoplethysmograph has at least two channels.

PPG pulses can be low-pass filtered, for example, at 0-40 Hz.

PPG pulses can also be obtained from the right foot of the infant or from the left foot of the infant.

The non-invasive technique provided by the present invention improves PDA diagnosis and monitoring for spontaneous closure or response to medical therapy. A continuous display of an index that correlates with left-to-right PDA shunting as provided by the present invention enables a clinician to monitor the ductus arterious for spontaneous closure, response to treatment, or re-opening of a previously closed ductus.

This invention will be better understood from the Experimental Details, which follow. However, one skilled in the art will readily appreciate that the specific methods and results discussed are merely illustrative of the invention as described more fully in the claims that follow thereafter.

Experimental Details

Subjects

The study was a prospective, single center study conducted in the neonatal intensive care unit of Cohen Children's Medical Center of New York from July 2013 to April 2015. The study was approved by the Institutional Review Board, and parental written informed consent was obtained prior to participant enrollment. The study population included preterm infants less than 32 completed weeks of gestation with a birth weight of less than 1500 grams who were diagnosed with a patent ductus arteriosus by standard echocardiography. Echocardiograms were requested by attending neonatologists based on clinical findings. Infants were excluded from the study if they had congenital heart disease.

The study was conducted with infants with echo-confirmed PDA with left-to-right R shunt that required medical or surgical treatment. After PDA closure, each infant served as its own control. Standard pulse oximeter probes were applied to the right hand (RH) and foot (F), and transmission infrared PPG signals were saved to a computer for waveform analysis. Amplitude was measured by digitally determining the maxima and minima of the systolic decrease of light transmission. Pulse transit time (PTT) (milliseconds [ms]) was determined from the R-wave of the ECG to the start of the systolic decrease of the PPG signal. Wilcoxon signed-rank test was used to compare the relative amplitude (rAM) and PTT before and after PDA closure.

The PPG Device and Recordings

PPG recordings were obtained at the time of diagnosis and again following either medical or surgical treatment. Post-operative recordings were obtained 24 hours after the end of general anesthesia and after discontinuation of inotropic support. The PPG waves were recorded simultaneously with the EKG tracing. Data collected on each infant included the following: blood pressure; pre and post-ductal oxygen saturation ($SpO_2$) and echocardiographic findings. Echocardiographic variables that were recorded included the size of the PDA, PDA:LPA ratio, LPA peak end-diastolic velocity, left ventricular ejection time and end diastolic volume, left atrial volume and the presence of reversal of flow in the descending aorta.

Neonatal pulse oximeter probes (Nellcor Neonatal SpO2 sensor, Covidien, Mansfield, Mass., United States) were applied to the right hand and foot. PPG waveforms were obtained using only the infrared light source in the oximeter probes, and the photodetector signals were directed to the PPG device (Lev Academic Center, Jerusalem, Israel). The PPG signals were low-pass filtered (0-40 Hz) to reduce high frequency noise, amplified, sampled at a rate of 1,000 samples per second with 16-bit resolution, and stored for further processing and analysis. A representative example of the hand and foot PPG signals before signal processing is shown in FIG. 1A. Light transmission through the hand and foot decreases during systole due to the increase in tissue blood volume; consequently, the maxima of the PPG signals occur at end-diastole.

Echocardiographic Measurements

The echocardiographic studies were performed using an Acuson Sequoia 512 (Siemens Medical Solutions USA, Inc., Malvern, Pa.) or Philips IE 33 (Philips Healthcare, Andover, Mass.). The following echocardiographic measurements were obtained and correlated with PPG parameters: left atrium diameter, aortic diameter, left pulmonary artery peak end diastolic velocity, and left ventricule shortening fraction, PDA diameter and left pulmonary artery diameter.

Signal Analysis

Figure 1B:
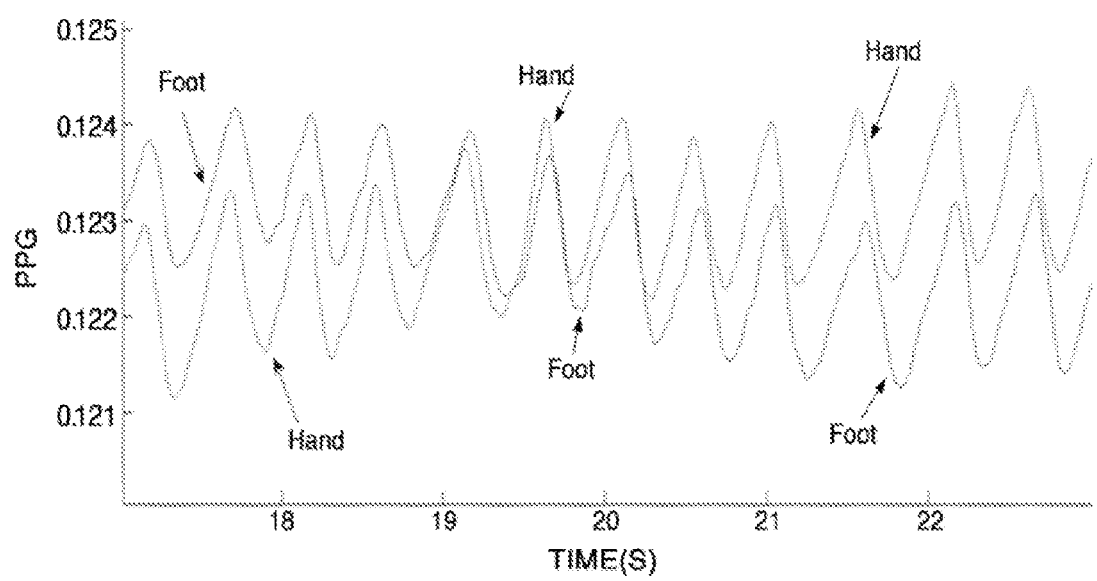
FIG. 1B. PPG curves from FIG. 1A after two smoothings.
Figure 2:
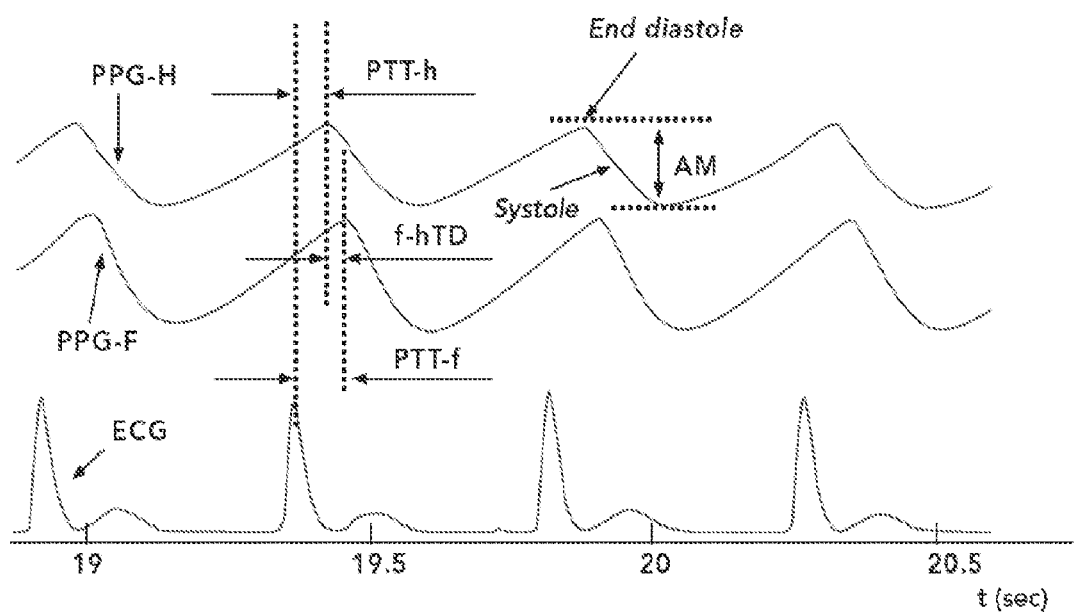
FIG. 2. Examples of photoplethysmographic (PPG) signals for the hand (H) and foot (F) and electrocardiogram (ECG) signals over time (t). PPG pulse amplitude (AM) is illustrated as the difference between the end-diastolic maximum and minimum of the systolic decrease of the pulse. The pulse transit time (PTT) is illustrated between an R wave of the ECG and the onset of the systolic decrease for the corresponding PPG pulse for the hand (PTT-h) and foot (PTT-f), as is the time delay between signals recorded at the hand and foot (f-hTD).
Figure 3A:
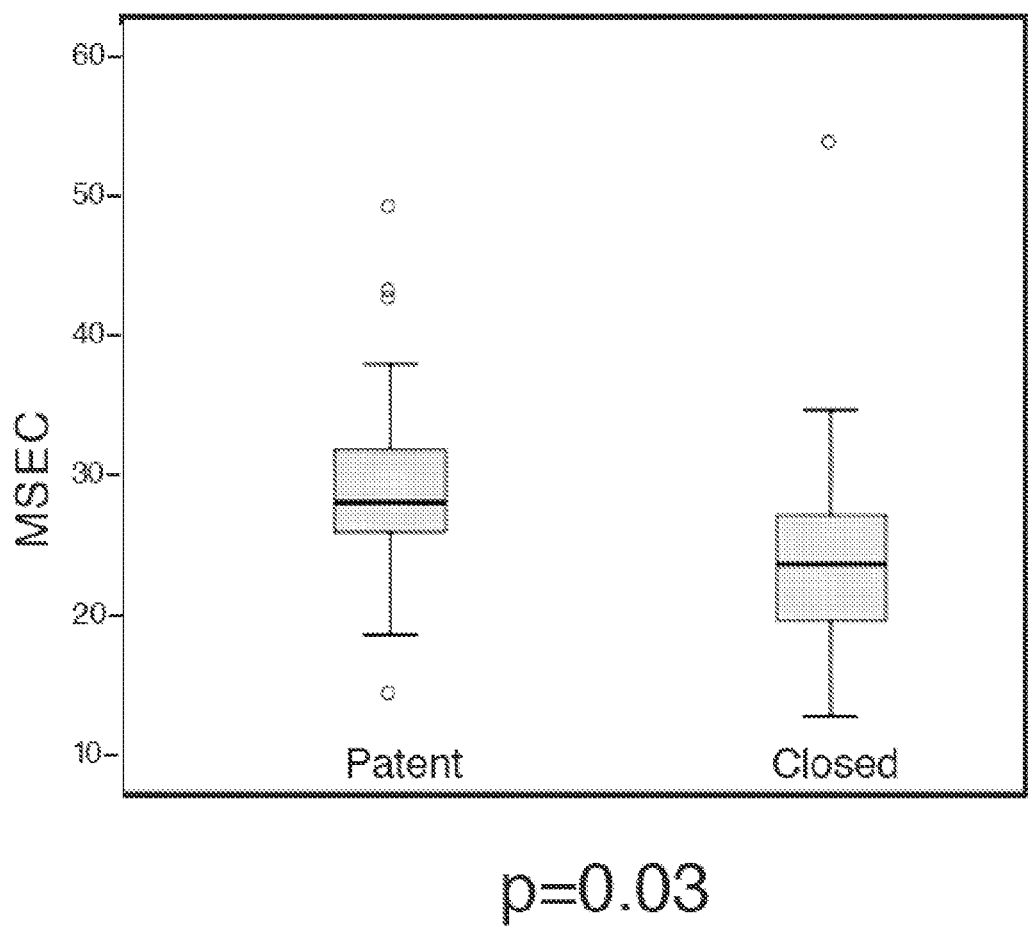
FIG. 3A. Boxplot distribution of time delay (msec) between PPG signals recorded at the hand and foot when the ductus arterious is patent or closed, p=0.03. Outlier values not included in the means are shown as open circles.
Figure 3B:
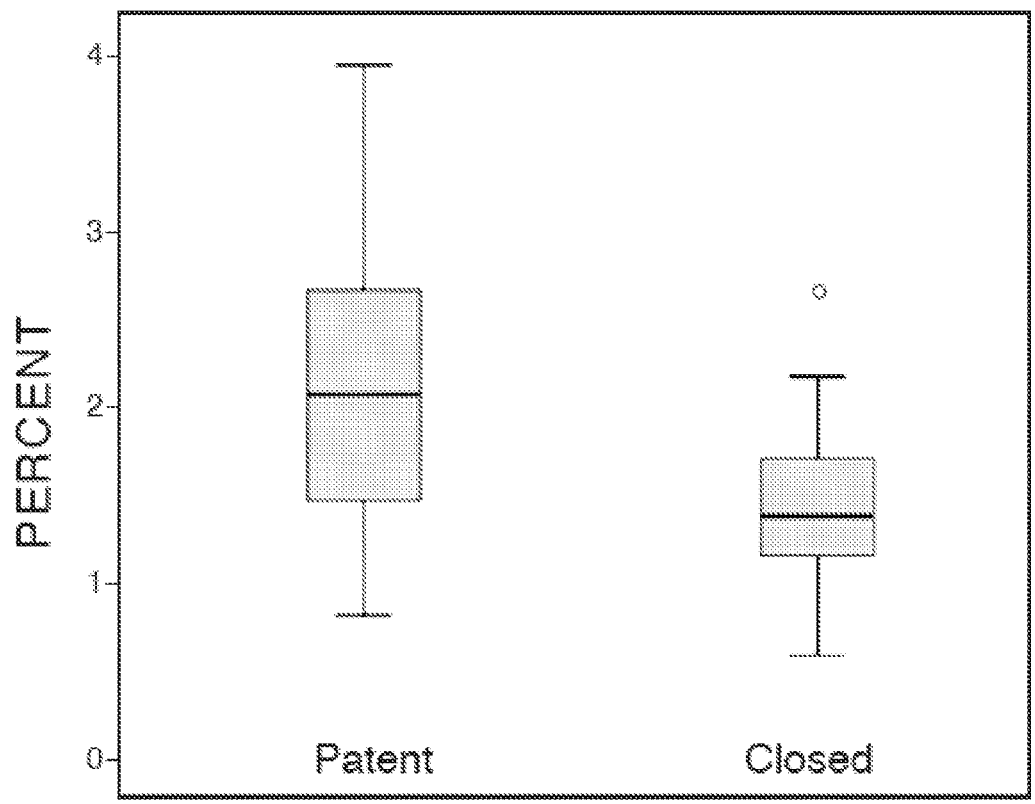
FIG. 3B. Boxplot distribution of relative pulse amplitude recorded at the hand when the ductus arterious is patent or closed, p=0.03. Outlier value not included in the mean is shown as an open circle.
Figure 3C:
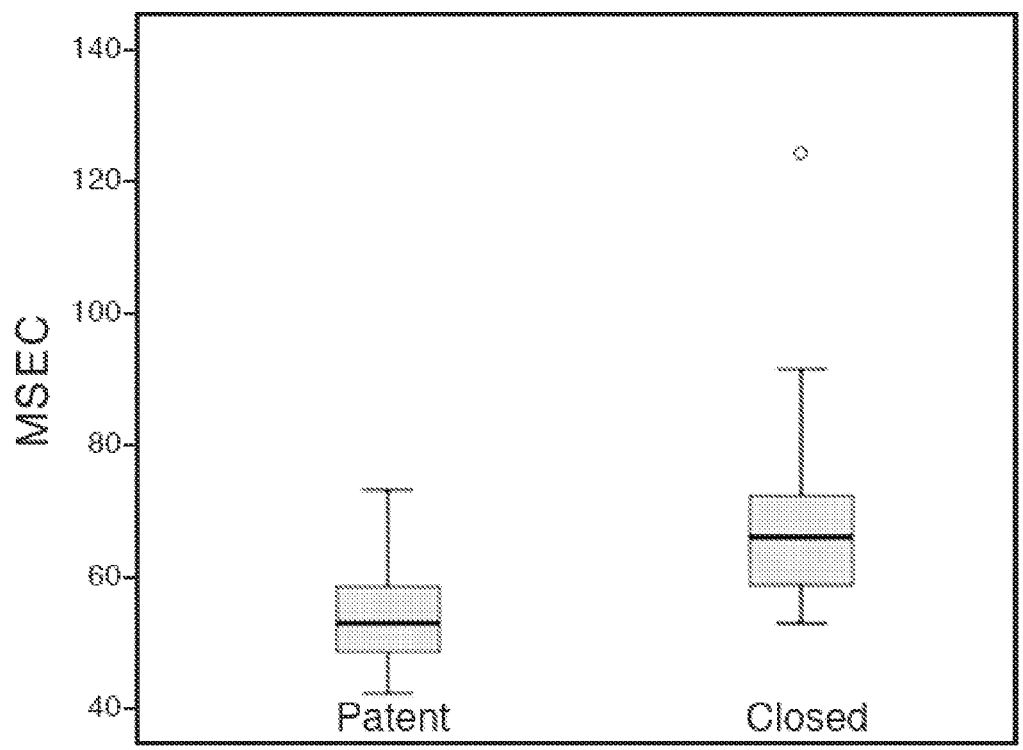
FIG. 3C. Boxplot distribution of pulse transit time (msec) recorded at the hand when the ductus arterious is patent or closed, p=0.01. Outlier value not included in the mean is shown as an open circle.
Figure 3D:
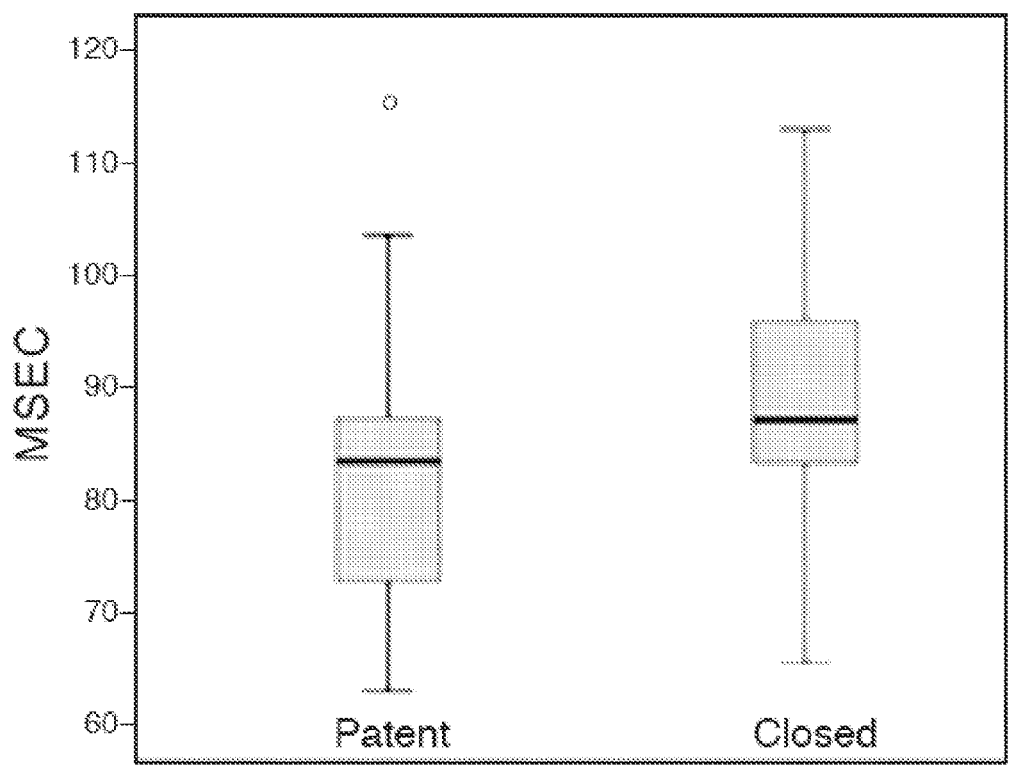
FIG. 3D. Boxplot distribution of pulse transit time (msec) recorded at the foot when the ductus arterious is patent or closed, p=0.03. Outlier value not included in the mean is shown as an open circle.
Figure 3E:
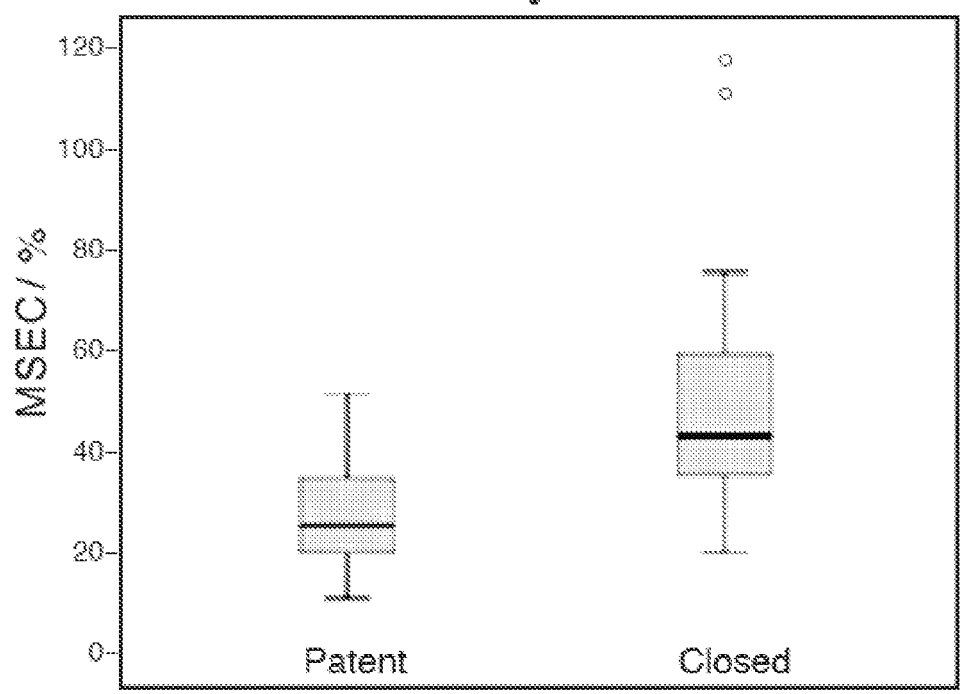
FIG. 3E. Boxplot distribution of the ratio of the pulse transit time (msec) recorded at the hand to the relative pulse amplitude recorded at the hand when the ductus arterious is patent or closed, p=0.03. Outlier values not included in the mean are shown as open circles.

In each PPG recording two regions of 10-20 PPG signals without motion artifact were selected. The hand and foot PPG signals were averaged with a 21 sample points moving average filter performed twice, serially. FIG. 1B depicts the waves of FIG. 1A after smoothing. The end-diastolic maxima and minima of systolic decrease were then digitally-identified and used to determine the following: pulse transit time (PTT) from the start of the R wave peak of the EKG to the amplitude of the pulse in the hand (PTT-h) and foot (PTT-f), time delay for the start of the systolic decrease between the foot and hand PPG pulses (f-hTD); and PPG pulse amplitude (AM), as illustrated in FIG. 2. The relative value of the latter (rAM) was defined as AM divided by the minimum of the PPG curve (minimum of systolic decrease); this value is proportional to the tissue blood volume increase in the foot or hand, respectively, during systole (Nitzan et al., 2009).

For each infant, the mean and standard deviation (SD) were calculated for the 10-20 PPG pulses for the PTT for the foot (PTT-F) and hand (PTT-H), rAM for the foot (rAM-F) and hand (rAM-H) and f-hTD. Values that deviated from the mean by 2SD or more (0-3 pulses for each parameter) were discarded. The means of rAM, PTT and f-hTD for each of the two regions in each recording were taken as the parameter values. All data were analyzed using IBM SPSS Statistics 22. Statistical significance was set at a p-value of 0.05. Results were expressed as mean±standard deviation. Statistical calculations using the paired t-test and Wilcoxon Signed Rank tests compared PTT-H, PTT-F, rAM-F, rAM-H and f-hTD between the neonates with open and closed ductus. Intra-subject variability of PTT, rAM and f-hTD results was assessed by taking the differences between the values of rAM, PTT and f-hTD divided by their means.

Results and Discussion

During the study period, 20 infants had either medical or surgical treatment for hemodynamically significant PDA. Of the 20 infants, 16 infants underwent surgical ligation and 4 infants were treated medically. EKG recordings were available for only 18 of the infants. Hence, rAM and f-hTD were calculated in 20 infants, but PTT which requires simultaneous EKG recordings were available for 18 infants before and after ductal closure. The mean (SD) gestational age at birth was 25 (1.37) weeks and the mean (SD) birthweight was 751 (172) g. The mean (SD) age at treatment was 27 (21) days and the mean (SD) weight at treatment was 1051 (520) grams. The average values for the rAM, PTT for the hand and foot and f-hTD are presented in Table 1. The range of PTT-H in open versus closed ductus was 47 to 72.8 ms (Mean±SD: 54.6±6.7 ms) versus 52.7 to 124.8 (Mean±SD: 69.1±16.9 ms), p=0.001. Similarly, the range of PTT-F in open versus closed ductus was 62.8 to 115.42 ms (Mean±SD: 81.95±13.3 ms) versus 65.3 to 112.7 (Mean±SD: 88.8±10.76 ms), p=0.03. The rAM-H pre- and post-ductal closure ranged from 0.79 to 3.27 versus 0.57 to 2.64 (Mean±SD: 2.04±0.71 vs 1.48±0.50), p=0.003. The range of the f-hTD prior to ductal closure was 14.6 to 49.4 ms (Mean±SD: 29.3±8.89 ms) and after ductal closure was 12.6 to 54.1 ms (Mean±SD: 24.82±8.67 ms), p=0.03. There was no significant difference in the mean values of the rAM-F before and after closure of the duct. For the patent and closed ductus, the distribution of f-hTD, rAM-H, PTT-H, PTT-F and PTT-H/rAM-H are depicted with means with standard deviations as boxplots in FIG. 3.

A summary of means and standard deviations of PTT-h, PTT-f, rAM-H, rAM-F and f-hTD for the patent and open ductus is provided in Table 2. To further differentiate the hemodynamic PPG indices before and after ductal closure, an index was calculated where the PTT-H was divided by the rAM-H. The results are shown in Table 3. The PTT-H increases and the rAM-H decreases after ductal closure and hence the index of PTT-H/rAM-H increases after ductal closure. PPG parameters related to PDA are summarized in Table 4. PTT-H, PTT-F, rAM-H/PTT-H, PTT-H/rAM-H, rAM-H and TD H-F are all significantly different in preterm infants following PDA closure.

PPG correlations with echocardiographic measurements are shown in Tables 5 and 6.

The non-invasive technique provided by the present invention improves PDA diagnosis and monitoring for spontaneous closure or response to medical therapy. A continuous display of an index that correlates with left-to-right PDA shunting as provided by the present invention enables a clinician to monitor the ductus arterious for spontaneous closure, response to treatment, or re-opening of a previously closed ductus.

TABLE 1

Upper and lower values of PPG parameters with mean and standard deviation

| | N | Minimum | Maximum | Mean | Std. Deviation |
|---|---|---|---|---|---|
| Patent f-hTD | 20 | 14.60 | 49.40 | 29.30 | 8.89 |
| Closed f-hTD | 20 | 12.60 | 54.10 | 24.83 | 8.67 |
| Patent rAM-H | 20 | 0.79 | 3.27 | 2.04 | 0.71 |
| Closed rAM-H | 20 | 0.57 | 2.64 | 1.48 | 0.50 |
| Patent rAM-F | 20 | 0.95 | 4.82 | 1.98 | 0.91 |
| Closed rAM-F | 20 | 0.39 | 3.62 | 1.61 | 0.88 |
| Patent rAM f/h | 20 | 0.61 | 2.13 | 1.04 | 0.47 |
| Closed rAM f/h | 20 | 0.47 | 3.10 | 1.11 | 0.60 |
| Patent PTT-H | 18 | 47.00 | 72.88 | 54.59 | 6.68 |
| Closed PTT-H | 18 | 52.70 | 124.48 | 69.12 | 16.88 |
| Patent PTT-F | 18 | 62.80 | 115.42 | 81.95 | 13.31 |
| Closed PTT-F | 18 | 65.30 | 112.70 | 88.80 | 10.76 |

TABLE 2

Summary of mean & standard deviation of PTT-h, PTT-f, rAM-H, rAM-F, f-hTD

| | PTT-h | PTT-f | rAM-h | rAM-f | h-fTD |
|---|---|---|---|---|---|
| PATENT | 54.6 ± 6.7 ms | 81.94 ± 13.31 ms | 2.04 ± 0.71% | 1.97 ± 0.91% | 29.31 ± 8.89 ms |
| CLOSED | 69.1 ± 16.9 ms | 88.8 ± 10.76 ms | 1.48 ± 0.5% | 1.61 ± 0.88% | 24.83 ± 8.67 ms |
| p-value | 0.001 | 0.03 | 0.003 | 0.07 | 0.03 |

TABLE 3

Ratio Predictors of Patent Ductus Arterious (PDA) (Mean values and SD)

| | PATENT | CLOSED | DELTA | p-VALUE |
|---|---|---|---|---|
| rAM-RH | 2.04 ± 0.71% | 1.48 ± 0.5% | −0.56 | P = 0.003 |
| PTT-RH | 54.6 ± 6.7 ms | 69.1 ± 16.9 ms | 14.5 | p = 0.001 |
| PTT-RH/ rAM-RH | 28.34 ± 10.54 ms/% | 50.89 ± 26.91 ms/% | 22.56 | p = 0.003 |
| rAM-RH/ PTT-RH | 39.99 ± 14.17%/s | 24.11 ± 10.44%/s | −15.89 | p = 0.0003 | rAM-RH: relative pulse amplitude for the right hand; PTT-RH: pulse transit time to the right hand.

TABLE 4

Changes in PPG Parameters after Closure of Ductus Arteriosus

| rAM-H | p = 0.003 | Decreased relative amplitude (rAM) in the hand (H) |
|---|---|---|
| PTT-H | p = 0.001 | Increased pulse transit time (PTT) from the heart to the hand |
| PTT-F | p = 0.03 | Increased pulse transit time from the heart to the foot (F) |
| TD H-F | p = 0.03 | Decreased time delay (TD) from hand to foot |
| PTT-H/ rAM-H | p = 0.003 | Increased ratio of pulse transit time from the heart to the hand/ relative amplitude in the hand |
| rAM-H/ | p = 0.0003 | Decreased ratio of relative |

TABLE 4-continued

Changes in PPG Parameters after Closure of Ductus Arteriosus

| PTT-H | amplitude in the hand to the pulse transit time from the heart to the hand |
|---|---|

TABLE 5

Echocardiographic characteristic of PDA

| Variables | Mean ± SD |
|---|---|
| Size of the PDA | 2.99 ± 0.83 |
| Restrictive/Non Restrictive | 100% non restrictive |
| PDA: Left Pulmonary Artery (LPA) | 0.89 ± 0.09 |
| Reversal in descending aorta | 100% |
| LPA peak end-diastolic velocity | 0.47 ± 0.15 m/sec |
| Left Atrium:Aorta (LA:Ao) diameter | 1.38 ± 0.48 |

TABLE 6

PPG Correlations with Echocardiographic Measurements in Infants with PDA (Pearson)

| | | |
|---|---|---|
| Left atrium diameter/Aorta diameter: rAM-F/H | r = 0.482 | p = 0.037 |
| Left atrium diameter/Aorta diameter: rAM-F | r = 0.495 | p = 0.031 |
| Left Pulmonary Artery peak end diastolic velocity: rAM-H | r = 0.538 | p = 0.014 |
| Left Ventricle Shortening Fraction: rAM - F/H | r = 0.559 | p = 0.030 |
| Left Ventricle Shortening Fraction: rAM - F | r = 0.539 | p = 0.038 |
| Left Ventricle Shortening Fraction: Rw - F/rAM - F | r = 0.488 | p = 0.077 |

PDA diameter: no correlation with PPG parameters
PDA diameter/left pulmonary artery diameter: no correlation with PPG parameters

REFERENCES

1. Allen J. Photoplethysmography and its application in clinical physiological measurement. Physiol Meas. 2007 March; 28(3):R1-39. Epub 2007 Feb. 20.
2. Elgendi M. On the analysis of fingertip photoplethysmogram signals. Curr Cardiol Rev. 2012 February; 8(1):14-25.
3. El Hajjar M, Vaksmann G, Rakza T, Kongolo G, Storme L. Severity of the ductal shunt: a comparison of different markers. Arch Dis Child Fetal Neonatal Ed. 2005 September; 90(5):F419-22.
4. Evans N, Iyer Parvathi. Longitudinal changes in the diameter of the ductus arteriosus in ventilated preterm infants:correlation with respiratory outcomes. Archives of Disease in Childhood 1995; 72: F156-F161.
5. Evans N et al. Diagnosis of the preterm patent ductus arteriosus: clinical signs, biomarkers, or ultrasound? Semin Perinatol. 2012a April; 36(2):114-22.
6. Evans N et al. Preterm patent ductus arteriosus: should we treat it? J Paediatr Child Health. 2012b September; 48(9): 753-8.
7. Goudjil S, et al. Noninvasive technique for the diagnosis of patent ductus arteriosus in premature infants by analyzing pulse wave phases on photoplethysmography signals measured in the right hand and the left foot. PLOS ONE June 2014, Vol. 9, issue 6, e98763, 9 pages.
8. Kluckow M, Evans N. Early echocardiographic prediction of symptomatic patent ductus arteriosus in preterm infants undergoing mechanical ventilation. J Pediatr. 1995 November; 127(5):774-9.
9. McNamara P J, Sehgal A. Towards rational management of the patent ductus arteriosus: the need for disease staging. Arch Dis Child Fetal Neonatal Ed. 2007 November; 92(6):F424-7.
10. Nitzan M., A. Babchenko, B. Khanokh and D. Landau. The variability of the photoplethysmographic signal—A potential method for the evaluation of the autonomic nervous system. Physiol. Meas. 1998, 19: 93-102.
11. Nitzan, M., Patron, A., Glik, Z., et al. Automatic non-invasive measurement of systolic blood pressure using photoplethysmography. BioMedical Engineering OnLine, 8: 28, 2009.
12. Noori S. Patent ductus arteriosus in the preterm infant: to treat or not to treat? Journal of Perinatology (2010) 30, S31-S37.
13. Oishi, M., Hishida, H., Kabe, K. and Hoshi, J. Monitoring neonatal peripheral circulation by electrocardiogram-to-oximeter pulse velocity. Pediatr. Res. 1993 33:653-57.
14. Sahni R. Noninvasive monitoring by photoplethysmography. Clin Perinatol. 2012 September; 39(3):573-83.
15. Sehgal A, McNamara P J. The ductus arteriosus: a refined approach! Semin Perinatol. 2012 April; 36(2):105-13.
16. Silverman N H, Lewis A B, Heymann M A, Rudolph A M. Echocardiographic Assessment of Ductus Arteriosus Shunt in Premature Infants. *Circulation.* 1974; 50:821-825.

What is claimed is:

1. A system for detecting patent ductus arteriosus (PDA) in an infant comprising a photoplethysmograph having one or more channels, one or more computing devices comprising one or more processors, a memory unit, a display device, and a computer-readable storage medium including computer-readable code that is read by the one or more processors to perform a method comprising the steps of:
   a) obtaining or receiving electrocardiogram (ECG) signals from the infant;
   b) obtaining or receiving photoplethysmographic (PPG) signals from a site on the upper body (UB) of the infant, and optionally from a foot (F) of the infant;
   c) determining, for each PPG pulse a PPG pulse amplitude (AM), the AM defined as an amplitude between the end-diastolic maximum and the consecutive systolic decrease minimum for the UB PPG pulses;
   d) determining the mean of two or more of the following parameters for a plurality of the PPG pulses:
      (i) a relative pulse amplitude (rAM) by dividing the AM by the systolic decrease minimum to obtain a rAM for the upper body (rAM-UB) PPG pulses;
      (ii) a pulse transit time (PTT-UB) between an R wave of the ECG and the onset of systolic decrease for the corresponding UB PPG pulse;
      (iii) a ratio PTT-UB/rAM-UB between the pulse transit time (PTT-UB) and the relative pulse amplitude for the UB (rAM-UB) PPG pulse;

(iv) a pulse transit time (PTT-F) between an R wave of the ECG and the onset of systolic decrease for the corresponding F PPG pulse; and
(v) a time delay (TD) between the onset of systolic decrease for the UB PPG pulse and the onset of systolic decrease for the corresponding F PPG pulse; and e) detecting patent ductus arteriosus (PDA) in the infant when two or more of:
1) the relative pulse amplitude for the UB (rAM-UB) is elevated above normal;
2) the pulse transit time (PTT-UB) is decreased below normal, and/or the pulse transit time (PTT-F) is decreased below normal, and/or the time delay (TD) of PPG pulses between the UB and F is elevated above normal; or
3) the ratio PTT-UB/rAM-UB is decreased below normal;
wherein the term "normal" refers to values of parameters obtained from infants with a closed ductus arteriosus.

2. The system of claim 1, wherein the steps further comprise one or more of selecting a section of PPG pulses without movement noise for analysis, low-pass filtering PPG signals to reduce high frequency noise, and smoothing PPG signals using a moving average filter.

3. The system of claim 1, wherein the photoplethysmograph has an infrared light source.

4. The system of claim 1, wherein in step d) a parameter from 10-20 pulses is averaged to obtain a mean.

5. The system of claim 1, wherein UB PPG signals are obtained or received from the right hand of the infant.

6. The system of claim 1, wherein UB PPG signals are obtained or received from the forehead or an earlobe of the infant.

7. The system of claim 1, wherein PPG signals are obtained or received from both the upper body (UB) and a foot (F) of the infant.

8. The system of claim 1, further comprising obtaining or receiving echocardiographic measurements from the infant and using one or more of the following parameters in combination with rAM-UB or in place of rAM-UB: ratio left atrium diameter/aorta diameter, left pulmonary artery peak end diastolic velocity, and left ventricle shortening fraction.

* * * * *